(12) United States Patent
Cedergreen (10) Patent No.: US 10,373,255 B1
(45) Date of Patent: Aug. 6, 2019

(54) METHODS AND SYSTEMS FOR MAINTAINING PHARMACY PROVIDER NETWORKS

(71) Applicant: Express Scripts, Inc., St. Louis, MO (US)

(72) Inventor: Jacob Jon Cedergreen, Saint Louis, MO (US)

(73) Assignee: Express Scripts Strategic Development, Inc., St. Louis, MO (US)

(*) Notice: Subject to any disclaimer, the term of this patent is extended or adjusted under 35 U.S.C. 154(b) by 277 days.

(21) Appl. No.: 13/780,073

(22) Filed: Feb. 28, 2013

Related U.S. Application Data (60) Provisional application No. 61/604,198, filed on Feb. 28, 2012.

(51) Int. Cl.
*G06Q 40/08* (2012.01)
*G06Q 50/22* (2018.01)

(52) U.S. Cl.
CPC ............ *G06Q 40/08* (2013.01); *G06Q 50/22* (2013.01)

(58) Field of Classification Search
CPC ........ G06Q 10/00; G06Q 50/22; G06Q 50/24; G06Q 40/08
USPC .......................................................... 705/2–3
See application file for complete search history.

(56) References Cited

U.S. PATENT DOCUMENTS

| | | | |
|---|---|---|---|
| 6,305,377 B1 * | 10/2001 | Portwood | G06F 19/3456 128/897 |
| 7,698,155 B1 | 4/2010 | Prasad et al. | |
| 7,711,583 B2 | 5/2010 | Epstein et al. | |
| 7,720,697 B1 | 5/2010 | Silverstein | |
| 8,055,511 B2 * | 11/2011 | McCallie | G06F 19/3456 705/2 |
| 8,386,274 B1 * | 2/2013 | Pinsonneault | 705/2 |
| 8,781,851 B2 * | 7/2014 | Anderson et al. | 705/2 |
| 2003/0167189 A1 * | 9/2003 | Lutgen et al. | 705/3 |
| 2004/0162740 A1 * | 8/2004 | Ericsson | G06Q 50/24 705/3 |
| 2006/0184391 A1 * | 8/2006 | Barre et al. | 705/2 |
| 2007/0043589 A1 * | 2/2007 | Warren et al. | 705/2 |

(Continued)

OTHER PUBLICATIONS

Member Central, "Pharmacy Networks," https://www.bluecrossma.com/wps/portal/members/using-my-plan/manage-my-plan/pharmacy-coverage/pharmacy-networks/!ut/p/c4/04_SB8K8xLLM9MSSzPy8xBz9CP0os_gwRzMPJzcPlwP_QHM3A09vc6-gUNdAY4Ngl_2CbEdFACJNLOw!/ downloaded on Feb. 27, 2013, pp. 1.

(Continued)

*Primary Examiner* — Sheetal R Paulson
(74) *Attorney, Agent, or Firm* — Dickinson Wright PLLC (57) ABSTRACT

Methods and systems for maintaining pharmacy provider networks are described. In one embodiment, claims adjudication data associated with a member and a prescribed drug is accessed. The prescribed drug associated with the member is classified as one of an acute medication and a maintenance medication. A pharmacy provider network is associated with the prescribed drug based on, at least in part, classifying the prescribed drug. It is determined if a pharmacy associated with the claims adjudication data is included within the pharmacy provider network associated with the prescribed drug. A pharmacy claim may be adjudicated for the prescribed drug based on the claim and the pharmacy provider network. Additional methods and systems are disclosed.

23 Claims, 5 Drawing Sheets

(56) References Cited

U.S. PATENT DOCUMENTS

| | | | | |
|---|---|---|---|---|
| 2007/0214009 A1* | 9/2007 | Epstein | ............... | G06F 19/3443 |
| | | | | 705/2 |
| 2008/0275738 A1* | 11/2008 | Shillingburg | ....... | G06F 19/3462 |
| | | | | 705/3 |
| 2009/0198517 A1* | 8/2009 | Ruben et al. | ..................... | 705/3 |
| 2012/0053960 A1* | 3/2012 | Gatti | ...................... | G06Q 10/00 |
| | | | | 705/2 |
| 2012/0253846 A1* | 10/2012 | John et al. | ......................... | 705/3 |

OTHER PUBLICATIONS

Florida Blue, "Pharmacy Coverage," http://www3.bcbsfl.com/wps/portal/bcbsfl/!ut/p/c0/04_SB8K8xLLM9MSSzPy8xBz9CP0os3gnA39DAwPHEEdXV3cnA89gr1AfZ88Al39nl_2CbEdFABaCju4!/?WCM_PORTLET=PC_7_B0O100ATAEEGB0ISJULCIP2CA3_WCM&WCM_GLOBAL_CONTEXT=/wps/wcm/connect/www_Content/si_bcbsfl/sa_employers/sa_ourplans/sa_pharmacycoverage/ct_emp_ourplans_pharmacy_benefitlistinghome, downloaded on Feb. 27, 2013, pp. 1-3.

United Healthcare, "Pharmacy Benefit Programs," http://consultant.uhc.com/assets/100-9999UHCPharmacyBenefitsASOSS4-11.pdf [p. 5], downloaded on Feb. 27, 2013, pp. 1-8.

BlueCross BlueShield of North Carolina, Specialty Pharmacy Networks Effective Jul. 1, 2011 Overview for BCBSNC Producers May 26, 2011, f.cfluent.com/f/3569/internet/1563_bcbs-specilaty-pharmacy-faqs.pdf, downloaded on Feb. 27, 2013, pp. 1-5.

PLOS One, Jul. 9, 2008, "Automated Identification of Acute Hepatitis B Using Electronic Medical Record Data to Facilitate Public Health Surveillance," http://www.ncbi.nlm.nih.gov/pmc/articles/PMC2440348/, downloaded on Feb. 27, 2013, pp. 1.

Wolters Kluwer Health—Medi-Span-Drug Indications Database, "Drug Indications Database," http://www.medispan.com/drug-indications-database.aspx, downloaded on Feb. 28, 2013, pp. 1-2.

IHomeMD—Drug Reference for Medical Conditions for iPhone . . . , "Itunes is the worlds easiest way to organise and add to your digital media collection." http://itunes.apple.com/ke/app/ihomemd-drug-reference-for/id427865188?mt=8, downloaded on Feb. 27, 2013, pp. 1-2.

* cited by examiner

METHODS AND SYSTEMS FOR MAINTAINING PHARMACY PROVIDER NETWORKS

CROSS-REFERENCE TO A RELATED APPLICATION

This application claims the benefit of U.S. provisional patent application Ser. No. 61/604,198, filed on 28 Feb. 2012, entitled "Methods and Systems for Maintaining Pharmacy Provider Networks," the entire disclosure of which is incorporated herein by reference.

FIELD

The field relates to pharmacy benefit plans, and more particularly to pharmacy networks for different prescription types.

BACKGROUND

Pharmacy benefit managers generally provide prescription drug programs for clients that may, for example, sponsor drug benefit programs for members. As part of the providing the prescription drug programs for clients, pharmacy benefit managers (PBM's) may adjudicate claims from pharmacies for prescriptions filled by members at various pharmacies. The PBM may also reimburse the pharmacies for prescriptions obtained by members at the pharmacies. The PBM may also bill clients for the cost of prescriptions adjudicated by the pharmacy benefit manager.

DETAILED DESCRIPTION

Example methods and systems for maintaining pharmacy provider networks are described. In the following description, for purposes of explanation, numerous specific details are set forth in order to provide a thorough understanding of example embodiments. It will be evident, however, to one of ordinary skill in the art that embodiments of the invention may be practiced without these specific details.

Generally, a client engages a pharmacy benefit manager (PBM) to offer a drug benefit program. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. The PBM may be a stand-alone PBM, or may be part of a larger organization that offers other benefits or services. In conjunction with receiving the co-pay (if any) from the member and dispensing the prescribed drug to the member, a pharmacy submits a claim to the PBM for the prescribed drug. The PBM may perform certain adjudication operations including verifying the eligibility of the member, reviewing the formulary to determine appropriate co-pay, coinsurance, and deductible for the prescribed drug, and performing a drug utilization review (DUR) on the member. In some embodiments, the PBM may determine and/or classify the prescribed drug and associate the drug with an acute medication pharmacy provider network or a maintenance medication pharmacy provider network.

The PBM may then provide a response to the pharmacy following performance of the aforementioned operations. As part of the adjudication, the client (or the PBM on behalf of the client) may ultimately reimburse the pharmacy for filling the prescribed drug when the prescription drug claim was successfully adjudicated. The aforementioned adjudication operations generally occur before the co-pay is received and the prescribed drug dispensed. However, the operations may occur simultaneously, substantially simultaneously, or in a different order. In addition, more or less adjudication operations may be performed as part of the adjudication process.

The methods and systems described herein may be used for maintaining pharmacy provider networks. In some instances, a prescriber, such as a doctor or other medical services provider, may prescribe a course of treatment that includes prescription drugs or medications. If the prescribed drug is to be used for a relatively short period of time, the prescribed drug may be referred to as an acute medication. Examples of acute medications may include, but are not limited to, anti-depressants, anti-viral mediations, muscle relaxants, antibiotics, and decongestants. If the prescribed drug is to be used for a relatively longer period of time and/or meets certain criterion, the prescribed drug may be referred to as a maintenance medication. The relatively short period of time and relatively long period of time may, in some embodiments, generally reflect the number of times that the prescription associated with the prescribed drug will be/has been filled. For example, a relatively short period of time may reflect that the prescribed drug is filled a single time or two times, while a relatively long period of time may reflect that the prescribed drug is filled more than two times. The number of fills associated with a relatively short period of time and a relatively long period of time may vary according to different embodiments and/or circumstances. In some instances, maintenance medication may be used to treat a chronic disease state and may be administered continuously rather than intermittently. Therapy with maintenance medication may not be considered curative or promoting of recovery. Some examples of maintenance medication may include, but are not limited to, hormone therapies, diabetes medication, heart medication, seizure medication, and osteoporosis medication.

In some instances, acute medication may be associated with a higher initial cost burden. For example, a pharmacy dispensing the prescribed drug for the patient may require the pharmacist to spend time obtaining information from the patient (e.g., benefit information, medical history, or the like) or educating the member about the prescribed drug. The cost associated with dispensing the prescribed drug may decrease with successive fills for the same prescribed medication for the same patient (e.g., if the medication is a maintenance medication), where the pharmacist typically spends less time educating the patient about the prescribed drug or gathering information associated with the patient, after initial consultations. For example, a pharmacist may initially (e.g., when the patient requests a first or second fill of the prescription) spend a similar amount of time obtaining information from the patient, educating the patient, etc., for prescriptions for maintenance medications and acute medications. However, after such initial time expenditure, the pharmacist may not be required to engage the patient in such depth for continuing refills of the maintenance medication.

In some embodiments, maintaining separate pharmacy provider networks may provide clients with more competitive reimbursement rates. These more competitive rates may reduced in reduced cost to patients for prescription drugs.

Figure 1:
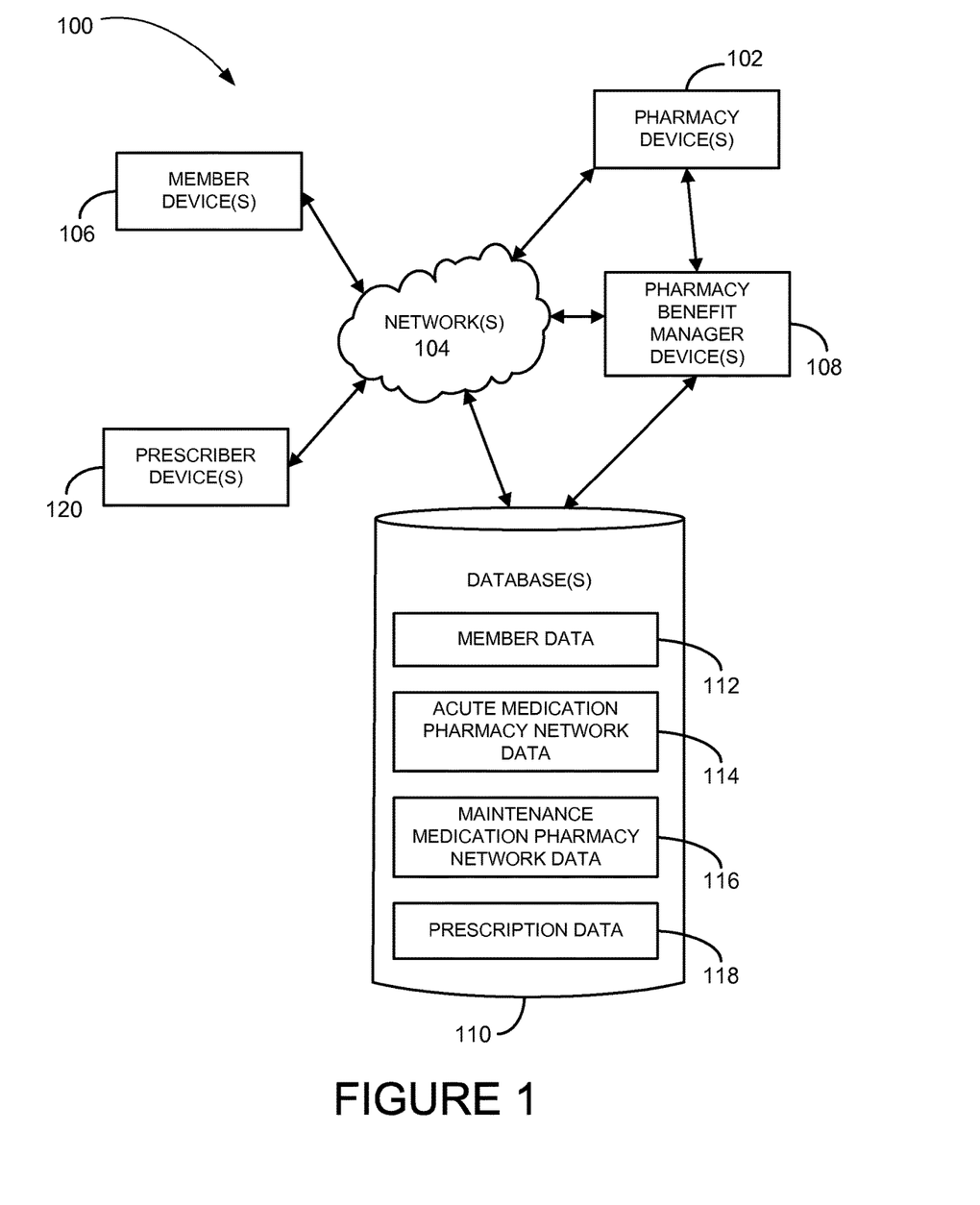
FIG. 1 is a block diagram of an example system, according to an example embodiment.

FIG. 1 is a block diagram of an example system 100, according to an example embodiment. The system 100 may include a pharmacy device 102 in communication over a network 104 with a member device 106. Similarly, one or more of the pharmacy device 102 and the member device 106 may be in communication with a pharmacy benefit manager device 108 over a network 104. Other devices may also be included.

In an embodiment, the pharmacy device 102 may be a device associated with the retail pharmacy location at which a patient attempts to obtain a prescribed drug. In some embodiments, the pharmacy device 102 may be associated with a mail order pharmacy or other drug dispensing location or service. The pharmacy device 102 may be utilized by the pharmacy, for example to submit a claim associated with a prescription to be filled to the PBM for adjudication. Additionally, in some embodiments, the pharmacy device 102 may enable reimbursement of the pharmacy by the PBM (e.g., on behalf of the client sponsoring the drug benefit program) for the prescription obtained by the patient.

The member device 106 may be a device operated by an entity that enables members of a drug benefit program offered by the PBM to access member benefits data and claims history data (e.g., for the member and the member's family). In some embodiments, the member device 106, alone and/or in conjunction with one or more other devices, may facilitate filling prescriptions (e.g., requesting prescription fills via a pharmaceutical delivery channel) by a member of a drug benefit program. In some embodiments, the member need not use the member device to obtain prescription drugs fills.

The pharmacy benefit manager device 108 is a device, or more than one device, operated by an entity at least partially responsible for the creation and/or management of drug benefit programs. While the pharmacy benefit manager device 108 is typically operated by a pharmacy benefit manager (PBM), other entities may operate the pharmacy benefit manager device 108 either on behalf of themselves, the PBM, or another entity. In some embodiments, a benefit manager that provides the drug benefit may also provide one or more than one additional benefits including a health benefit, a dental benefit, a vision benefit, a wellness benefit, a radiology benefit, a pet care benefit, an insurance benefit, a long term care benefit, a nursing home benefit, and the like.

In general, a client engages a PBM to offer a drug benefit program. A person who is a participant or member of a drug benefit program offered by the client may obtain prescription drugs according to pricing, pharmacy selection, rebates, discounts and the like provided by the terms of the drug benefit program. The PBM may offer various therapy implementation programs that may impact the pricing, pharmacy selection, rebased, discounts, and the like, provided to members of the drug benefit plan.

The client's offered drug benefit program may be a stand-alone drug benefit operated by the PBM, or as part of a health care benefit operated by a health insurance company where the PBM services are offered directly by the health insurance company or offered indirectly by the PBM on behalf of the health insurance company.

The PBM may service a variety of people in a single drug benefit program, multiple drug benefit programs, or may otherwise service people. In some embodiments, the pharmacy benefit manager device 108 may be generally capable of analyzing claim adjudication data associated with members to identify one or more prescribed drugs associated with the member. In some embodiments, the claim adjudication data may be received through an adjudication request for a pharmacy claim. In some embodiments, the adjudication request may be received from a pharmacy device 102.

The pharmacy benefit manager device 108 (and/or another device) may be in communication directly (e.g., through local storage) and/or through the network 104 (e.g., in a cloud configuration or software as a service) with a database 110. The database 110 may be deployed, in whole or in part, on one or more of the pharmacy device 102, the member device 106, the pharmacy benefit manager device 108 and/or on another device. The database 110 may store one or more of member data 112, acute medication pharmacy network data 114, maintenance medication pharmacy network data 116, and/or prescription data 118.

The member data 112 may include information regarding members of the drug benefit program. In general, the member data 112 may include various data regarding members of a drug benefit program administered by the PBM. For example, the member data 112 may include member name, member contact information (e.g., address, telephone number, email address, and the like), member health related information, member demographic information. In some embodiments, the member data may include member claims data for claims that have been adjudicated for each member of a drug benefit program (e.g. prescribed drugs, prescription history, pharmacy usage, co-pay information, and the like). The member data 112 may include current and/or historical claims adjudication data for members of the drug benefit program, including prescriptions filled by a member, number of fills of each prescription for the member, dates of fills of each prescription for the member, drug utilization reviews for each prescription for the member, an identification of each pharmacy at which each fill of each prescription was obtained, and the like.

The acute medication pharmacy network data 114 may include data associated with an acute medication pharmacy network. Such data may include, for example, pharmacy providers that belong to an acute medication pharmacy network associated with a drug benefit program, costs associated with the acute medication pharmacy network and with pharmacy providers that belong to the acute medication pharmacy network, criterion for establishing a prescribed drug as an acute medication, and the like.

The maintenance medication pharmacy network data 116 may include data associated with maintenance medication pharmacy network. Such data may include, for example, pharmacy providers that belong to a maintenance medication pharmacy network, costs associated with the maintenance medication pharmacy network and with pharmacy providers that belong to the maintenance medication pharmacy network, criterion for establishing a prescribed drug as a maintenance medication, and the like.

Prescription data 118 may include data associated with prescriptions filled by one or more members of the drug benefit program, for example, an identification of the member and the prescribed drug, an identification of one or more pharmacies at which a prescription, or more than one prescriptions, for the drug have been filled, an identification of the dates on which the prescription(s) have been filled, a quantity of drug filled, an identification of the healthcare professional that prescribed the drug, and the like. In some embodiments, the prescription data 118 may include prescription drug claims that have submitted to the PBM by one or more pharmacies and/or prescription drug claims that have been adjudicated by the PBM. As such, the prescription data 118 may include information collected and/or utilized in connection with adjudicating a pharmacy claim for a prescription. The prescription data 118 may also include the results of adjudicating a claim (e.g., claim approval, claim denial, as well as any additional information). The prescription data 118 may include prescription data that maybe stored by one or more devices in FIG. 1.

A prescriber device 120 may also be coupled to the network 104 for communication with one or more other devices, such as the pharmacy device 102, the member device 106, and the pharmacy benefit manager device 108. The prescriber device 120 may be operated by, or on behalf of, a medical care professional that may prescribe a course of treatment that may include a prescribed drug for a member. In some embodiments, the prescriber device 120 may be utilized by the medical care professional to transmit a prescription associated with a patient (who may be a member of the drug benefit program) to a pharmacy (e.g., via the pharmacy device 102) and/or to the pharmacy benefit manager device 108. The pharmacy, to which the prescription may be transmitted, may be a retail pharmacy location, a mail order pharmacy, or another type of drug dispensing facility.

In the system 100, the pharmacy device 102, the member device 106, and/or the prescriber device 120 may communicate with the pharmacy benefit manager device 108 to enable a member to have a prescription filled through a pharmaceutical delivery channel. The pharmaceutical delivery channel may include, for example, a retail pharmacy location, a mail order pharmacy service, or other drug dispensing service. In some embodiments, the prescriber device 120 may be used to send and receive information including the prescription data 118 associated with a member. The person operating the member device 106 may be a member of a drug benefit plan operated by the PBM, and who has a drug prescribed to them by a medical healthcare professional, and/or may be an individual (such as a family member, care giver, or the like) who may operate the member device 106 on behalf of the individual who has received a prescription for a drug. The member device 106 may be associated with a single member, or multiple members. A member may use multiple member devices 106.

Examples of the network 104 by which the pharmacy device 102, the member device 106, the pharmacy benefit manager device 108, and the prescriber device 120 may communicate with one or more of each other may include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Other conventional and/or later developed wired and wireless networks may also be used.

While the system 100 in FIG. 1 is shown to include single devices 102, 106, 108, and 120, multiple devices may be used. Examples of the devices 102, 106, 108, and 120 include a server computer, a personal computer, a laptop or notebook computer, a mobile computing device (such as a smartphone, a tablet computing device, a personal digital assistant (PDA), or the like), a display device, a generic or specialized computing system, a gaming unit, or the like. Other devices may also be used. The devices 102, 106, 108, and 120 may each be the same type of device, or may be different types of devices.

Additionally, while the system 100 is shown to include a single network (i.e., the network 104) in FIG. 1 multiple networks may be used. The multiple networks may communicate with one another, e.g., as in series to link the devices 102, 106, 108, 120, or in parallel to link the devices 102, 106, 108, 120.

Figure 2:
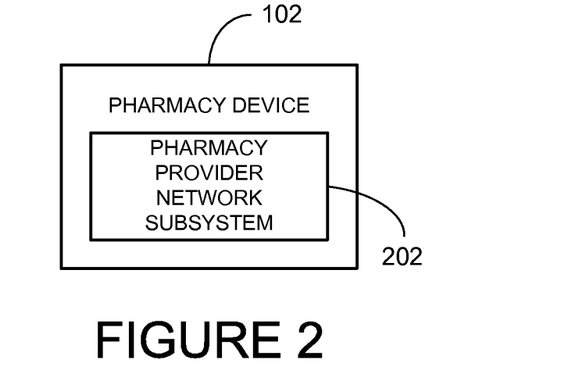
FIG. 2 illustrates an example pharmacy device that may be deployed in the system of FIG. 1, according to an example embodiment.

FIG. 2 illustrates the pharmacy device 102, according to an example embodiment. The pharmacy device 102 may be deployed in the system 100, and/or may be otherwise deployed. The pharmacy device 102 may be used by a device operator to submit claims information to the pharmacy benefit manager device 108. The claims information may be associated with a prescription that a member is attempting to fill at the pharmacy operating the pharmacy device 102. The claims information may be submitted (e.g., via transmission between the pharmacy device 102 and the pharmacy benefit manager device 108) to the pharmacy benefit manager device 108 for adjudication of the claim, e.g., to determine eligibility and coverage of the prescription under the drug benefit program, the deductible amount for which the member is responsible, and the like.

The pharmacy device 102 may include a pharmacy provider network subsystem 202. In general, the pharmacy provider network subsystem 202 may enable a PBM to associate an identified prescribed drug with the appropriate pharmacy provider network. For example, in some embodiments the pharmacy provider network subsystem 202 may allow a PBM to identify a particular prescription for a particular drug as being a prescription for an acute medication. In some embodiments, the pharmacy provider network subsystem 202 may allow a PBM to identify a particular prescription for a particular drug as being a prescription of a maintenance medication. In some embodiments, the pharmacy provider network subsystem 202 may allow a PBM to associate prescriptions for acute medications with an acute medication provider network. In some embodiments, the pharmacy provider network subsystem 202 may allow a PBM to associate prescriptions for maintenance medications with a maintenance medication provider network. Further, in some embodiments the pharmacy provider network subsystem 202 may allow a PBM to establish acute medication provider networks including specifically and/or generally identified pharmacies, and to establish maintenance medication provider networks including specifically and/or generally identified pharmacies. In some embodiments, the pharmacy provider network subsystem 202 may allow a PBM to establish eligibility and/or coverage benefits for prescriptions of acute medications and maintenance medications filled at pharmacies included within acute medication provider networks or maintenance medication provider networks.

Figure 3:
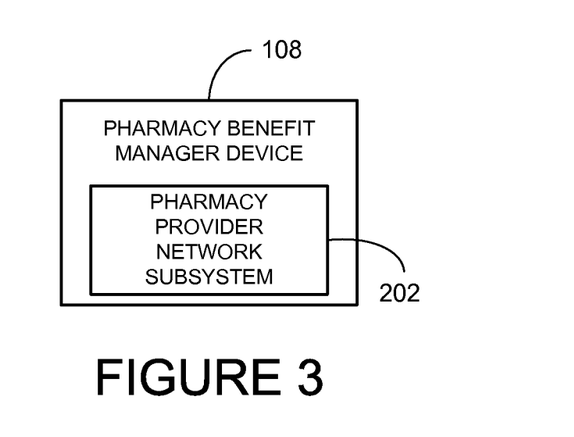
FIG. 3 illustrates an example pharmacy benefit manager device that may be deployed in the system of FIG. 1, according to an example embodiment.

FIG. 3 illustrates the pharmacy benefit manager device 108, according to an example embodiment. The benefit manager device 108 may be deployed in system 100 and/or may be otherwise deployed. In general, the pharmacy benefit manager device 108 may allow a PBM to receive claims information (e.g., from a pharmacy device 102 via the network 104) from a pharmacy. The claims information may be associated with a prescription submitted to the pharmacy by a member of a drug benefit program administered by the PBM. The claims information may allow the PBM to adjudicate the claim of the prescription, e.g., to determine eligibility of the member, review the formulary, determine appropriate co-pay by the member for the prescription, perform drug utilization review, and/or to perform other pharmacy claims adjudication functions.

The pharmacy benefit manager device 108 may include a pharmacy provider network subsystem 202. In some embodiments, the pharmacy provider network subsystem 202 included within the pharmacy benefit manager device 108 may provide server-side functionality to the pharmacy device 102. By way of example, the pharmacy provider network subsystem 202 may be deployed in the pharmacy device 102 and the pharmacy benefit manager device 108. In some embodiments, the pharmacy device 102 may perform a portion of the operations described herein, and the PBM device 108 may perform a portion of the operations described herein. In some embodiments, all of the functionality of the pharmacy provider network subsystem 202 may be provided by the pharmacy device, may be provided by the pharmacy benefit manager device 108, or may be provided by another device.

Figure 4:
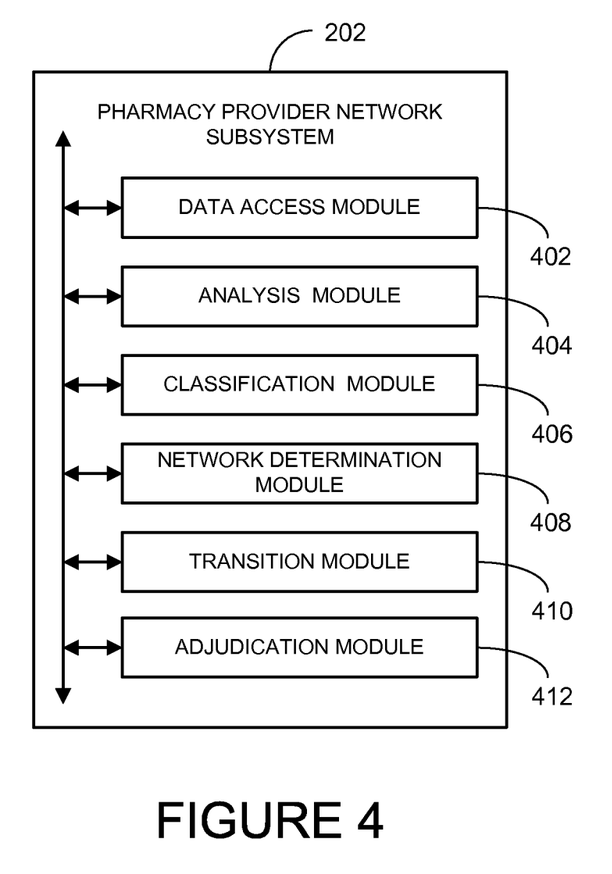
FIG. 4 is a block diagram of an example separate pharmacy provider network subsystem that may be deployed within the pharmacy device of FIG. 2 and/or the pharmacy benefit manager device of FIG. 3, according to an example embodiment.

FIG. 4 illustrates an example pharmacy provider network subsystem 202 that may be deployed in the pharmacy device 102, the pharmacy benefit manager device 108, or otherwise deployed in another system. One or more modules are communicatively coupled and included in the pharmacy provider network subsystem 202 to enable association of a prescribed drug with the appropriate pharmacy provider network. The modules of the pharmacy provider network subsystem 202 that may be included are a data access module 402, an analysis module 404, a classification module, 406, a network determination module 408, a transition module 410, and an adjudication module 412. Other modules may also be included.

In some embodiments, the modules of the pharmacy provider network subsystem 202 may be distributed so that some of the modules are deployed in pharmacy device 102 and some modules are deployed in the pharmacy benefit manager device 108. One, or more than one, of the module of the pharmacy provider network subsystem 202 may be deployed in another device. In one embodiment, the modules are deployed in memory and executed by a processor coupled to the memory. The functionality contained within the modules 402-412 may be combined into a lesser number of modules, further divided among a greater number of modules, or redistributed among existing modules. Other configurations including the functionality of the modules 402-412 may be used.

In some embodiments, the data access module 402 may access claims adjudication data of a member. Claims adjudication data may be associated with each pharmacy claim that is submitted for prescriptions of a member. For example, when a member of a drug benefit program attempts to fill a prescription, the pharmacy at which the member attempts to fill the prescription may transmit various information to the PBM (e.g., between pharmacy device 102 and pharmacy benefit manager device 108) for adjudication of the claim for the prescription. The claims adjudication information may include, for example, an identification of the member for whom the claim is being submitted, and identification of the medication and dosage being prescribed, an identification of the prescribing healthcare professions, etc. As generally discussed above, the PBM may utilize the claim information to determine eligibility and coverage for the prescription, conduct drug utilization review, determine reimbursement rate to the pharmacy, and the like. In an embodiment, the claim information may be the pharmacy claim itself, additional/alternative information, or both. The claims adjudication data for a member may include various additional information and the PBM may perform various additional operations and/or reviews as part of the claim adjudication process.

In some embodiments, claims adjudication data may be accessed by the data access module 402 at the time when a request to fill a prescription is made at a pharmacy by a member. For example, when the member attempts to fill a prescription the member may submit the prescription to the pharmacist (e.g., by either physically submitting a written prescription and/or by directing a prescribing healthcare profession to transmit an electronic prescription to the pharmacy or to the pharmacist). In such an instance, a device operator of the pharmacy device 102 submits an adjudication request to the PBM relative to the prescription. In an embodiment, the adjudication request may include the pharmacy claim itself, submitted to the PBM by the pharmacy. For example, the device operator of the pharmacy device 102 may enter the claims adjudication data (or a portion of the claims adjudication information) into pharmacy device (e.g., via manual entry, scanning a written prescription, or transmitting an electronic prescription to the pharmacy device 102) into and/or via the pharmacy device 102. In such an embodiment, the data access module 402 may access the claims adjudication data (and/or a portion of the claims adjudication data) based on a received adjudication request (e.g., which may include claims adjudication data entered into and/or via the pharmacy device 102) including receiving the entered claims adjudication data.

In some embodiments, the data access module 402 may access claims adjudication data (e.g., which may be included as part of the prescription data 118, in some embodiments) from the database 110. In some embodiments, the data access module 402 may access claims adjudication data by accessing the member data 112 from the database 110, and/or by receiving the claims adjudication data (which may include receiving the member data 112) from another device. Receiving the member data 112 may include, for example receiving the member data 112 through the network 104 form the pharmacy device, the pharmacy benefit manager device 108, or from a different device. In some embodiments, the data access module 402 may access claims adjudication data by receiving claims data entered into, or via, the pharmacy device, and by accessing the member data 112 included within the database 110.

In some embodiments, the data access module 402 may access the claims adjudication data in response to a request to adjudicate a claim on behalf of a member of a drug benefit program. For example, when the member attempts to fill a prescription at a pharmacy, the pharmacy may transmit claims adjudication data (e.g., information that may be used as part of the claims adjudication process) to the PBM. In response to the claims adjudication data being transmitted to the PBM, the data access module 402 may access claims adjudication data associated with the member attempting to fill the prescription. In some embodiments, the data access module 402 may access all claims adjudication data associated with the member, for example, which may include claims adjudication data associated with the prescription the member is attempting to fill as well as claims adjudication data associated with prescriptions that the member has previously filled. In some embodiments, the data access module 402 may access all claims adjudication data associated with the prescription that the member is attempting to fill and/or associated with the prescription that the member is attempting to fill and associated with previous prescriptions for the same drug that have been filled by the member. In some embodiments, the data access module 402 may access all claims adjudication data associated with the member relative to the pharmacy at which the member is attempting to fill the prescription. The pharmacy may include a retail pharmacy location or a mail-order pharmacy. In some embodiments, the data access module 402 may access various combinations of the above claims adjudication data.

In some embodiments, the analysis module 404, may analyze the claim adjudication data of a member to identify a prescribed drug associated with the member. For example, the analysis module 404 may parse the claims adjudication data to determine the drug associated with one, or multiple, pharmacy claims that have been submitted for adjudication by the PBM on behalf of a member. That is, whenever a pharmacy claim is submitted by a pharmacy to the PBM for adjudication, the pharmacy claim includes an identification of the drug. The identification of the drug may be included as a component of the claims adjudication data (e.g., which may be accessed by the data access module 402). The analysis module 404 may analyze the claim adjudication data accessed by the data access module 402 and may determine the drug associated with the member and at least one claim adjudication on behalf of the member.

As generally discussed above, the claim adjudication data accessed by the data access module 402 may include claim adjudication data for a prescription that the member is attempting to fill, claim adjudication data for prescriptions that the member had previously filled, and both the prescription that the member is attempting to fill and prescriptions that the member had previously filled. Accordingly, in some embodiments, the analysis module 404 may identify the drug of a prescription the member is attempting to fill, the drug of prescriptions that the member has previously filled, and/or both the drug of a prescription the member is attempting to fill and drugs of prescriptions that the member has previously filled. In some embodiments, in addition to identifying drugs associated with one, or more than one, prescriptions that the member is attempting to fill or has previously filled, the analysis module 404 may determine the number of times that the member has filled prescriptions for the various drugs. In some embodiments, the analysis module 404 may also determine the dates on which the member filled prescriptions for the various drugs.

In an example embodiment, the analysis module 404 may identify a prescribed drug that a member is attempting to fill, and may generate a message to be transmitted to the member that the member has to fill the identified drug within either the acute medication pharmacy provider network or the maintenance medication pharmacy provider network.

In some embodiments, a classification module 406 may classify identified prescribed drug associated with a member as being either an acute medication or as being a maintenance. For example, the analysis module 404 may identify one, or several, prescriptions associated with a member of a drug benefit program (e.g., based on claims adjudication data accesses by the access module 402). The classification module 406 may classify one, or more than one, of the prescriptions associated with the member as being an acute medication or as being a maintenance medication. By way of illustrative example, three prescribed drugs may be associated with a member. The member may have received prescriptions for each of the three drugs from a prescribing healthcare professional (e.g., which prescriptions may have been received by one or more of the pharmacy device 102 and the pharmacy benefit manager device 106, either via user entry of prescription data, scanning of a prescription, or transmission of an electronic prescription from prescriber device 120), and/or the member may have filled or attempted to fill each of the three prescriptions at a pharmacy (e.g., which may have submitted associated claims to the PBM for each prescription). One of the three prescribed drugs may be an antibiotic that was newly prescribed by a healthcare professional. The classification module 406 may determine that the antibiotic is an acute medication. The other two prescribed drugs associated with the member may be a heart medication and a diabetes medication. The classification module 406 may classify each of the heart medication and the diabetes medication as maintenance medications.

In an embodiment, the classification module 406 may classify prescriptions associated with the member based on one, or more than one, classification rules. The one, or more than one, classification rules may be based on, for example, a drug type or drug category, the specific prescribed drug, on a number of refills/duration of treatment specified by the prescription, or the like. As such, the classification rules may be based on attributes of the prescribed drugs (e.g., specific drug, drug type, drug category, or the like), and/or may be based on attributes associated with a course of treatment or administration of the drugs (e.g., the duration of treatment, number of refills anticipated and/or number of fills actually requested for the prescription or drug, which may span multiple separate prescriptions).

In some embodiments, the classification rules may be based on whether the prescription indicates a number of refills during a specified time period, a number a refills requested by the member (e.g., within a specified time period), or the like. For example, a classification rule may specify that three or more refills of a drug and/or prescription is classified as a maintenance medication. In a situation in which a prescription indicates that six refills of a prescription are available (e.g., three or more refills), the classification module 406 may classify the prescription and/or the drug as being a maintenance medication for the member as the number of refills may exceed an acute medication threshold number of fills (or fill requests). Similarly, if a member attempts to refill a prescription for a drug for a third time (or attempts to get a fill of a drug for which the member has received two fills of the same drug within a specified period of time), the classification module 406 may classify the drug as a maintenance medication. As such, the classification module 406 may classify the drug as a maintenance medication when a first fill of a prescription is requested (e.g., if the prescription indicates that three or more fills are available), or may classify the drug as a maintenance medication when a member requests a third or subsequent refill of the medication. With respect to the latter example, the classification module 406 may initially classify a drug as an acute medication (e.g., when the first and second fills of the prescription are requested by the member). Further, upon the member requesting a third fill of the prescription, the classification module 406 may classify the drug as a maintenance drug.

While the foregoing example has related to the classification of a drug as being a maintenance medication if three, or a greater number, of refills are requested, this is intended only for the purpose of illustration, as the threshold number of refills may vary for classifying a drug as a maintenance medication, and/or classification rules unrelated to the number of fills or refills of a prescription may be utilized. Additionally, in some embodiments, some drugs may be classified as a maintenance drug based on the specific drug, the drug category, the drug type, or the like. In some such embodiments, drugs classified as maintenance medications may be classified as maintenance medications for all members of a drug benefit program. In some embodiments (for example, including embodiments in which a drug may be classified based on a number of fills), a drug may be classified as a maintenance medication with respect to only a specific member of a drug benefit program. In such an embodiment, the classification of drugs as an acute medication or a maintenance medication may occur on a member-by-member basis.

In some embodiments, the classification module 406 may classify a prescribed drug associated with a pharmacy claim of an adjudication request as an acute medication or a maintenance medication. In some embodiments, the classification module 406 may access one or more other data sources, such as a web server, database or other storage device to access information used to classify identified prescribed drug.

In some embodiments, the network determination module 408 may use the classification provided by the classification module 406 to determine or select which pharmacy provider network to associate with the classified prescribed drug. For example, if the classification module 406 classifies the drug as an acute medication, the network determination module 408 may associate the prescribed drug for the member with an acute medication pharmacy network. In an embodiment in which the classification module 406 classifies the drug as a maintenance medication, the network determination module 408 may associated the prescribed drug for the member with a maintenance medication pharmacy network.

In some embodiments, the network determination module 408 may determine if a pharmacy at which a fill of the prescription drug is requested is a pharmacy associated with an acute medication pharmacy provider network, or if the pharmacy at which the fill of the prescription drug is requested is a pharmacy associated with a maintenance medication pharmacy provider network. In some embodiments, the network determination module may access the acute medication pharmacy network data 114 and/or the maintenance medication pharmacy network data 116 from the database 110. In some embodiments, accessing the acute and/or maintenance medication pharmacy network data 114/116 may include receiving the data from the database 110. Receiving the data 114, 116 from the database may include receiving the data 114, 116 over the network 104 from the pharmacy device, the member device 106, the pharmacy benefit manager device 108, or from another device. The network determination module 408 may compare the pharmacy at which the request for the fill of the prescription is made to the pharmacies included in the acute/maintenance pharmacy network data 114/116.

In some embodiments, the transition module 410 may be used to transition a prescribed drug associated with a member from one pharmacy provider network to a different pharmacy provider network. For example, the transition module 410 may transition a prescribed drug associated with a member from an acute medication pharmacy provider network to a maintenance medication pharmacy provider network. Transitioning a prescribed drug associated with a member from an acute medication pharmacy provider network to a maintenance medication pharmacy provider network may include associating different member benefits for fills of the prescribed drug at pharmacies within the acute medication pharmacy provider network than the benefits associated with fills of the prescribed drug at pharmacies within maintenance pharmacy provider network. The different member benefits may be the co-pay required by the member for fills of the prescription, coverage eligibility of fills of the prescription by the member, or other member benefits provided for fills of the prescription under the drug benefit program. The difference in member benefits provided for fills of the prescription at acute medication pharmacy provider network pharmacies as compared to member benefits provided for fills of the prescription at a maintenance medication pharmacy provider network pharmacy may motivate the member to seek fills at pharmacies within one network rather than the other, e.g., by requiring a higher co-pay, or denying coverage eligibility for fills of the prescription at pharmacies of one provider network, denying coverage at one provider network, or the like.

For example, a member receive a prescription (e.g., from a prescribing healthcare professions) and may fill the prescription at a pharmacy included within an acute medication pharmacy provider network. The prescription may initially be classified as an acute medication by the classification module 406 (e.g., based on one or more classification rules). As such, the network determination module 408 may associate the prescription with the acute medication pharmacy provider network, and the transition module 410 may associate a first set of member benefits for fills of the prescription by the member at the pharmacy within the acute medication pharmacy provider network. Subsequently (e.g., in response to the member seeking additional fills of the prescription and/or fills of subsequent prescription for the same drug within a specified time period or the like), the classification module 406 may classify the prescription for the drug as a maintenance medication (e.g., based on one, or more than one, classification rules).

In response to the classification module 406 classifying the prescription as a maintenance medication, the network determination module 408 may associate the prescription for the drug with a maintenance pharmacy provider network. In response to the network determination module 408 associating the prescription drug with a maintenance pharmacy provider network, the transition module 410 may associated a modified set of benefits with the member for fills of the prescription at pharmacies within an acute medication pharmacy provider network. For example, the transition module 410 may associate a first set of benefits with the member for fills of the prescription at pharmacies within an acute medication pharmacy provider network. The transition module 410 may further associated a second set of benefits with the member for fills of the prescription at pharmacies within a maintenance medication pharmacy provider network.

For example, first set of benefits may include a denial of coverage (or an elevated co-pay, or other benefits) for fills of the prescription at pharmacies within the acute medication pharmacy provider network, and the second set of benefits may include full covers (or a lower co-payor other benefits) for fills of the prescription at pharmacies within the maintenance medication pharmacy provider network. Accordingly, the difference between the first set of benefits and the second set of benefits may motivate the member to seek fills of the medication at pharmacies within the maintenance medication pharmacy provider network. In some embodiments, the transition module 410 may transmit a warning to the member attendant to associating the first set of benefits with fills of the prescription at pharmacies within the acute medication pharmacy provider network. For example, the member may be permitted a single additional fill (and/or partial fill) of the prescription before the first set of benefits are associated with fills of the prescription at pharmacies within the acute medication pharmacy provider network. Such a warning may be transmitted, for example, to the pharmacy device 102, wherein the warning may be conveyed to the member by the operator of the pharmacy device. As such, the member may not experience a lapse in the prescription while the member seeks out fills of the prescription at a pharmacy within a maintenance medication pharmacy provider network consistent with the second set of member benefits.

In some embodiments, multiple pharmacy provider networks may be available for members. For example, actions associated with filling a prescription for an acute medication may be different than actions associated with filling a maintenance medication. In either the acute or the maintenance medication pharmacy provider networks, there may be different costs associated with the different networks. For example, costs may be influenced by agreements between the PBM and pharmacies within the maintenance medication pharmacy provider networks and between the PBM and pharmacies within the acute medication pharmacy provider networks. For example, agreements between the PBM and pharmacies within the maintenance medication pharmacy provider network may provide for a lower reimbursement rate (of the pharmacy by the PBM) for maintenance drugs dispensed for member by the pharmacies within the maintenance medication pharmacy provider network than for maintenance drugs dispensed for members by pharmacies within the acute medication pharmacy provider network. For example, different agreements may result from different fulfillment costs borne by the pharmacies in fulfilling member prescriptions at pharmacies within the maintenance medication pharmacy provider network as compared to pharmacies within the acute medication pharmacy provider network.

The adjudication module 414 may adjudicate the claim received from the pharmacy by the adjudication request module. For example, the pharmacy claim for the prescription fulfilled for the member may be adjudicated, which may in some embodiments include operations such as conducting a DUR relative to the prescription, determining member coverage, etc. In some embodiments, the adjudication module may adjudicate the pharmacy claim for the prescribed drug based on the claim and the pharmacy provider network in which the pharmacy submitting the claim is included. In an embodiment in which the prescription drug may be classified as a maintenance medication and the pharmacy may be determined to be included within an acute medication pharmacy provider network, the claim may be adjudicated using the first set of member benefits (e.g., the set of member benefits for prescriptions for maintenance medications filled at pharmacies included within acute medication pharmacy provider networks). Upon successful adjudication of the claim by the adjudication module, the PBM may approve the claim. In some embodiments, the adjudication module may also transmit an adjudication response based on the adjudication of the claim. In some embodiments, the warning transmitted by the transition module 410 may be transmitted with, and/or as part of, the adjudication response.

Figure 5:
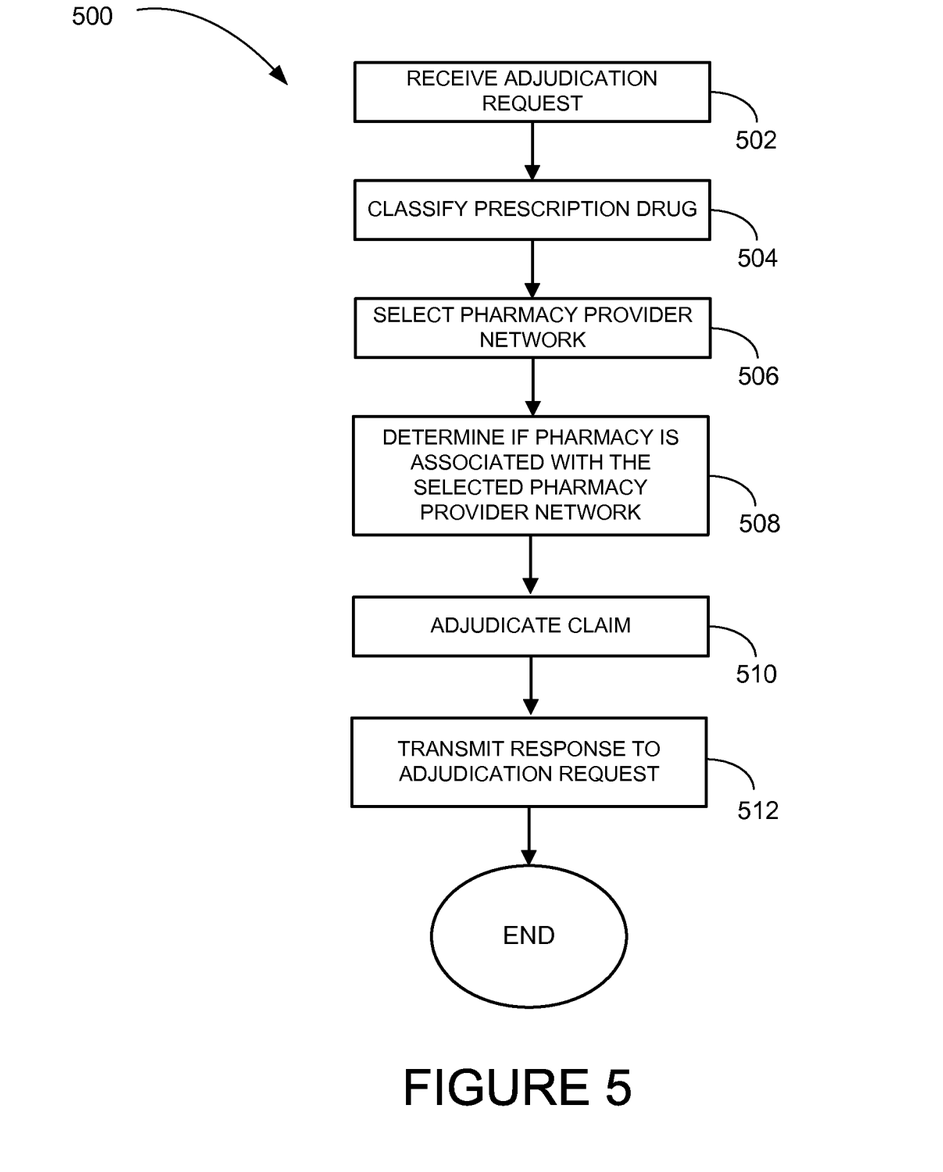
FIG. 5 is a block diagram of a flowchart illustrating a method for maintaining pharmacy provider networks, according to an example embodiment.

FIG. 5 illustrates a method 500 for maintaining pharmacy provider networks, according to an example embodiment. The method 500 may be performed by the pharmacy benefit manager device 108, partially by the pharmacy benefit manager device 108 and partially by the pharmacy device 102, or may be otherwise performed.

An adjudication request may be received at block 502. The adjudication request may be associated with a current adjudication request and/or a previous or historical adjudication request. For example, receiving the adjudication request may include accessing claim adjudication data. Claims adjudication data may be received or retrieved from the database 110. For example, claims adjudication data may be included, at least in part, in the member data 112 included within database 110. In some embodiments, the claims adjudication data may be received from the pharmacy device 102. In some embodiments, an adjudication request may be received from the pharmacy benefits manager device 108. The adjudication request may include a pharmacy claim associated with a member, a prescribed drug, and a pharmacy. In some embodiments, the claims adjudication data may be access through other sources, such as data feeds from different healthcare provider vendors, servers, databases, or the like.

The prescribed drug associated with the adjudication request may be classified at block 504. In some embodiments, the claim adjudication data associated with the member may be analyzed to identify any prescribed drugs associated with the member. The identified prescribed drugs may include newly prescribed drugs, existing prescribed drugs, past prescribed drugs, and the like. The identified prescribed drug may be classified as acute medication or maintenance medication. In some embodiments, the identified prescribed drug may be classified using one, or more than one, classification rules. Classifying the identified prescribed drug as either an acute medication or a maintenance medication may include determining a number of refills (e.g., a number of available refills and/or a number of refills that have been requested) for the prescribed drug. In some embodiments, classifying the prescribed drugs may include comparing the number of refills for the prescribed drugs to a threshold number of refills. In some embodiments, all prescribed drugs may be classified as acute medications by default, and may be classified as maintenance medications when one, or more than one, maintenance medication criterion are met (e.g., a determination of a drug type, a drug classification, a threshold number of fills, a threshold number of available refills, or the like).

In some embodiments, a pharmacy provider network may be selected, at block 506, based on the classified prescribed drug. In some embodiments, if the prescribed drug is classified as an acute medication, then an acute medication pharmacy provider network may be selected. In some embodiments, if the prescribed drug is classified as a maintenance medication, then a maintenance medication pharmacy provider network may be selected.

In some embodiments, the prescribed drug may be associated at block 506 with either an acute medication pharmacy provider network or a maintenance medication pharmacy provider network in response to the classification of the prescribed drug. In some embodiments, the acute medication pharmacy provider network may include a retail pharmacy and/or a mail order pharmacy. In some embodiments, the maintenance medication pharmacy provider network may include a retail pharmacy and/or a mail order pharmacy.

In some embodiments, a determination is made whether the pharmacy associated with the adjudication request is associated with the selected pharmacy provider network at block 508. Determining if the pharmacy associated with the adjudication request (e.g., the pharmacy at which a request to fill a prescription is made by a member) may include accessing acute medication pharmacy network data 114 and/or accessing maintenance medication pharmacy network data 116. If the pharmacy associated with adjudication request is included in the acute medication pharmacy network data 114, it may be determined that the pharmacy associated with the adjudication request is included in the acute medication pharmacy provider network. If the pharmacy associated with the adjudication request is included within the maintenance medication pharmacy network data 116, it may be determined that the pharmacy associated with the adjudication request is included within the maintenance medication pharmacy provider network.

In some embodiments, the pharmacy associated with the adjudication request may be a retail pharmacy. In some embodiments, the pharmacy associated with the adjudication request may be a mail-order pharmacy. In some embodiments, the pharmacy may not be associated with a pharmacy provider network. If the pharmacy associated with the adjudication request is not associated with a pharmacy provider network, one or more pharmacies that are associated with the selected pharmacy provider network may be provided or generated. In some embodiments, the one or more pharmacies that are associated with the selected pharmacy provider network may be provided or identified as a suggested alternative pharmacy.

In some embodiment, if the pharmacy is determined to be associated with the selected pharmacy provider network, (e.g., the prescription is determined to be for an acute medication and the pharmacy is included within an acute medication pharmacy provider network, or the prescription is determined to be for a maintenance medication and the pharmacy is included within a maintenance medication pharmacy provider network) the pharmacy claim associated with the adjudication request may be adjudicated on behalf of the member. In some embodiments, the pharmacy claim associated with the adjudication request may not be adjudicated until a request to proceed with the adjudication is received or approved.

In some embodiments, if the prescription is for a drug classified as a maintenance medication (e.g., if the number of refills for a prescribed drug associated with the adjudication request exceeds a set threshold for number of refills, or based on other classifying criterion) the requested fill and/or any additional refills may need to be refilled at a pharmacy in or associated with the maintenance medication pharmacy provider network (for example, in order for the PBM to receive best pricing for the member). For example, if a prescription has refills beyond the first fill (e.g., a second fill), the member may be required to fill the additional fills at a pharmacy in the maintenance medication pharmacy provider network to obtain best pricing for the member. In some embodiments, the maintenance medication pharmacy provider network may include a subset of pharmacies in the acute medication pharmacy provider network.

In some embodiments, the pharmacy claim may be adjudicated at block 510. For example, the pharmacy claim for the prescription that the member is attempting to fill may be adjudicated, which may in some embodiments include operations such as conducting a DUR relative to the prescription, determining member coverage, etc. In some embodiments, the adjudication module may adjudicate the pharmacy claim for the prescribed drug based on the claim and the pharmacy provider network in which the pharmacy submitting the claim is included. In an embodiment in which the prescription drug may be classified as a maintenance medication and the pharmacy may be determined to be included within an acute medication pharmacy provider network, the claim may be adjudicated using the first set of member benefits (e.g., the set of member benefits for prescriptions for maintenance medications filled at pharmacies included within acute medication pharmacy provider networks).

In some embodiments, a response to the adjudication request may be generated and transmitted at block 512. In some embodiments, the response to the adjudication request may include the classification of the prescribed drug, the selected pharmacy network, the data associated with the adjudication of the pharmacy claim, or any combination thereof. If the pharmacy associated with the adjudication request is not associated with the selected pharmacy provider network, a message stating that the pharmacy is not a part of the selected pharmacy network may be transmitted to the pharmacy device 102 and/or the member device 106. In some embodiments, the response may include a list of suggested or alternative pharmacies associated with the selected pharmacy network may also be included.

In some embodiments, different member benefits for the prescription under the drug benefit program may be associated with pharmacies included within the acute medication pharmacy provider network and with pharmacies included within the maintenance medication pharmacy provide network. For example, the different benefits for the prescription may include different costs (e.g., co-pay, coverage eligibility, etc.) to the member associated with filling a prescription for a maintenance medication at a pharmacy within the acute medication pharmacy provider network as compared to the costs to the member associated with filling the prescription at a pharmacy within the maintenance medication pharmacy provider. The difference in the member benefits for the prescription under the drug benefit program may motivate the member to seek fills of prescriptions for a maintenance medication at a pharmacy included within the maintenance medication pharmacy provider network.

In some embodiments, the costs associated with the acute medication pharmacy provider network or the maintenance medication pharmacy provider network may include co-pays, reimbursement rate, billed rate, or any combination thereof. In some embodiments, the reimbursement rate for the provider may be the pay rate to the pharmacy provider (e.g. the pharmacy fulfilling the prescription of the member) for purchasing the prescribed drug and dispensing the prescribed drug to the member. In some embodiments, the billed rate to the client or client affiliates is the rate that the client is charged for dispensing the prescribed drug to the member by the pharmacy or provider. In some embodiments, the spread may be the difference between the billed rate to the client and the reimbursement rate for the pharmacy provider.

Other factors that may influence or affect costs associated with pharmacy provider networks may include explicit administrative fees that may be charged, rebates prescribed drug or tasks associated with the process of dispensing the prescribed drug to members, or bulk discount rates for prescribed drugs obtained by providers.

Figure 6:
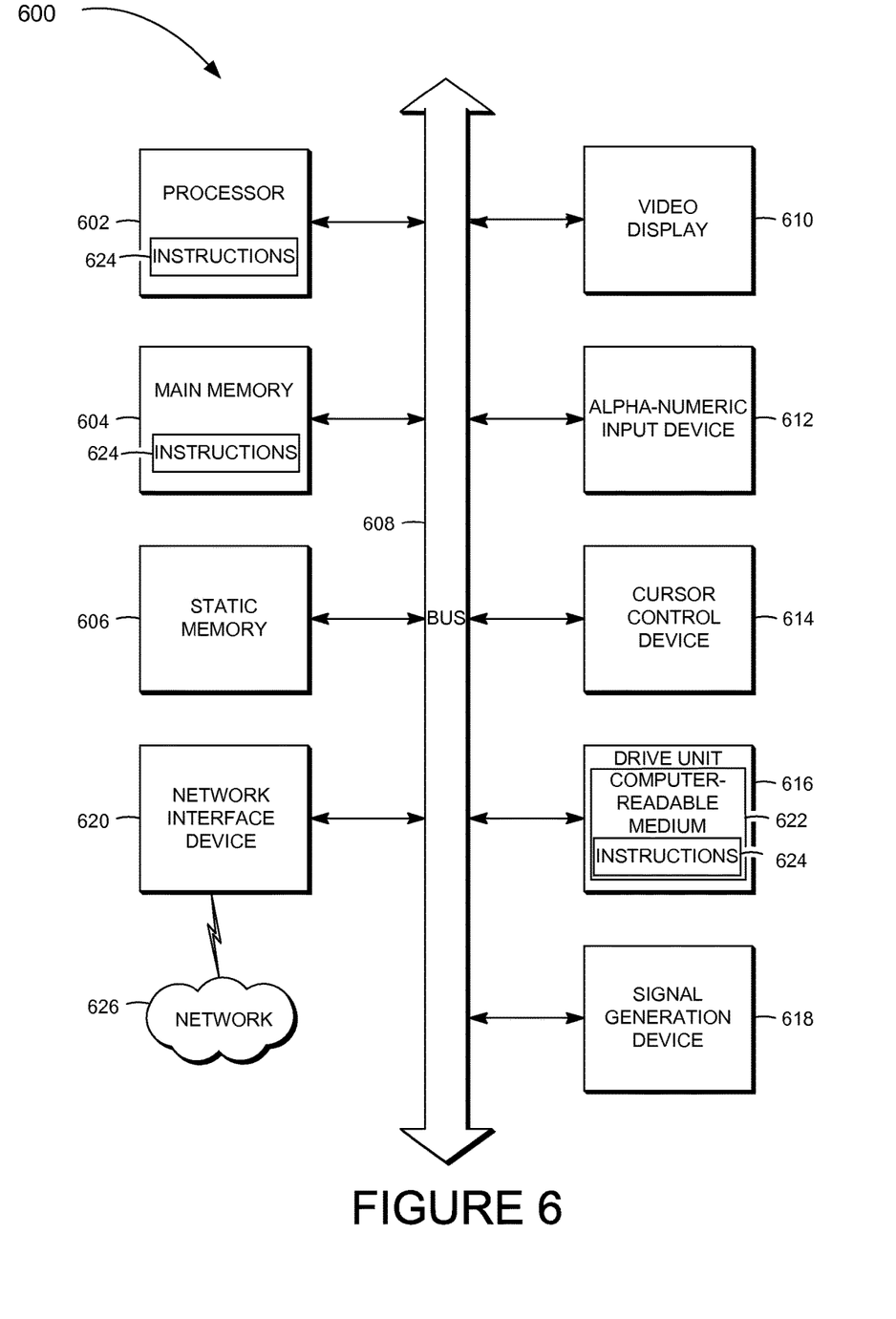
FIG. 6 is a block diagram of a machine in the example form of a computer system within which a set of instructions for causing the machine to perform any one or more of the methodologies discussed herein may be executed.

FIG. 6 shows a block diagram of a machine in the example form of a computer system 600 within which a set of instructions may be executed causing the machine to perform any one or more of the methods, processes, operations, or methodologies discussed herein. The member device 106 and/or the pharmacy benefit manager device 108 may include the functionality of the one or more computer systems 600.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 600 includes a processor 602 (e.g., a central processing unit (CPU) a graphics processing unit (GPU) or both), a main memory 604 and a static memory 606, which communicate with each other via a bus 608. The computer system 600 may further include a video display unit 610 (e.g., a liquid crystal display (LCD) or a cathode ray tube (CRT)). The computer system 600 also includes an alphanumeric input device 612 (e.g., a keyboard), a cursor control device 614 (e.g., a mouse), a drive unit 616, a signal generation device 618 (e.g., a speaker) and a network interface device 620.

The drive unit 616 includes a computer-readable medium 622 on which is stored one or more sets of instructions (e.g., software 624) embodying any one or more of the methodologies or functions described herein. The software 624 may also reside, completely or at least partially, within the main memory 604 and/or within the processor 602 during execution thereof by the computer system 600, the main memory 604 and the processor 602, also constituting computer-readable media. In some embodiments, the computer-readable medium 622 is a non-transitory computer-readable medium.

The software 624 may further be transmitted or received over a network 626 via the network interface device 620.

While the computer-readable medium 622 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, optical media, and magnetic media.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In one embodiment, claims adjudication data associated with a member and a prescribed drug may be accessed. The prescribed drug associated with the member may be classified as one of an acute medication and a maintenance medication. A pharmacy provider network may be associated with the prescribed drug based on, at least in part, classifying the prescribed drug. It may be determined if a pharmacy associated with the claims adjudication data is included within the pharmacy provider network associated with the prescribed drug. A pharmacy claim may be adjudicated for the prescribed drug based on the claim and the pharmacy provider network.

In an embodiment, a pharmacy claim to adjudicate is received. The pharmacy claim is associated with a member and a prescribed drug may be received. The prescribed drug associated with the member may be classified as a maintenance medication. It may be determined that a pharmacy associated with the request to adjudicate the pharmacy claim is included within an acute medication pharmacy provider network. A warning that the a modified set of member benefits are associated with filling the prescribed drug at the pharmacy may be transmitted based on the classification of the prescribed drug as a maintenance medication and a determination that the pharmacy is included within the acute medication pharmacy provider network.

While the methods and systems are generally described herein within the context of acute pharmacy provider networks and maintenance pharmacy provider networks, other types or classification of pharmacy provider network may be made. Additionally, while the method and systems are generally described herein within the context of prescription drugs and pharmacies, the principles herein may be equally applied to claims under drug benefit programs, or other healthcare programs administered by a PBM or a healthcare program provider. Examples of other such programs may include benefits for care, testing, and treatment associated with medication professional visits, medical lab work, hospitals, and clinics.

Thus, methods and systems for maintaining pharmacy provider networks have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method for communicating over a network to fill a prescription comprising:
    retrieving via electronic communication from a memory, on a processor of a pharmacy benefit manager, the memory being remote from the processor, claims adjudication data associated with a member and a prescribed drug stored in the memory;
    determining, on the processor of the pharmacy benefit manager, whether a number of available fills of the prescribed drug exceeds an acute medication threshold number of available fills that is variable and remotely selectable, wherein the acute medication threshold number is stored in a remote database and set in a pharmacy benefit provided by a client in a prescription drug plan to the member;
    classifying, on the processor of the pharmacy benefit manager, the prescribed drug associated with the member as one of an acute medication and a maintenance medication based on the determination of whether the number of available fills of the prescribed drug exceeded the acute medication threshold number of available fills;
    associating, on the processor, the prescribed drug with a type of pharmacy provider network based on classification of the prescribed drug, the type of pharmacy provider network being divided into two distinct subsets of an acute medication pharmacy provider network or a maintenance medication pharmacy provider network for the acute medication and the maintenance medication, respectively;
    determining, on the processor, whether a pharmacy associated with the claims adjudication data is included within the type of pharmacy provider network associated with the prescribed drug;
    adjudicating, on the processor, a pharmacy claim for the prescribed drug through the pharmacy based on the pharmacy claim, the adjudication data and a determination of whether the pharmacy is included within the type of pharmacy provider network;
    transmitting, from the processor over a network, an adjudication response from adjudication based adjudicating the pharmacy claim;
    receiving, at a pharmacy device of the pharmacy at the acute medication pharmacy provider network or the maintenance medication pharmacy provider network that is associated with the prescription, the adjudication response;
    authorizing a filling of the prescription for the member at the pharmacy after receipt of the adjudication response associated with the member; and
    filling the prescription at the pharmacy after receipt of the adjudication response.

2. The method of claim 1, wherein accessing the claims adjudication data includes receiving an adjudication request from a pharmacy relative to the prescribed drug for the member.

3. The method of claim 1, wherein accessing the claims adjudication data includes accessing historical claims adjudication data for the member.

4. The method of claim 1, wherein classifying the prescribed drug comprises:
    analyzing the claims adjudication data to determine one or more of a drug attribute and a fill attribute associated with the prescribed drug.

5. The method of claim 1, wherein classifying the prescribed drug comprises:
    identifying one of a drug identity, a drug type, and a drug category.

6. The method of claim 1, wherein classifying the prescribed drug comprises:
    determining that a number of fill requests of the prescribed drug exceeds an acute medication threshold number of fill requests.

7. The method of claim 6, wherein the acute medication threshold number of fill requests is three or greater; and
    wherein adjudicating includes transitioning the prescription from the acute medication pharmacy provider network and the maintenance medication pharmacy provider network when the acute medication threshold number is exceeded and filling the prescription using the maintenance medication pharmacy provider network with a different member benefit than a member benefit at the acute medication pharmacy provider network.

8. The method of claim 1, further comprising:
    associating a first set member benefits with the prescribed drug for the acute medication pharmacy provider network; and
    associating a second set of member benefits with the prescribed drug for the maintenance medication pharmacy provider network.

9. The method of claim 1, wherein accessing the claims adjudication data includes accessing historical claims adjudication data for the member.

10. The method of claim 1, wherein the acute medication pharmacy provider network includes specifically identified pharmacies including a retail pharmacy and wherein the maintenance medication pharmacy provider network includes specifically identified pharmacies including a retail pharmacy and a mail-order pharmacy.

11. The method of claim 1, further comprising transmitting a message to the member that the prescription must be filled at the pharmacy within the type of pharmacy provider network associated with the prescribed drug.

12. A non-transitory machine-readable medium storing instructions for filling a prescription over a network, which, when executed by one or more processors, cause the one or more processors to:
    selecting a variable number for an acute medication threshold number of available fills for each drug available in the network;
    access claims adjudication data associated with a member and a prescribed drug;
    determine whether a number of available fills of the prescribed drug exceeds the acute medication threshold number of available fills using the claims adjudication data;
    classify the prescribed drug associated with the member as one of an acute medication and a maintenance medication based on the determination of whether the number of available fills of the prescribed drug exceeded the acute medication threshold number of available fills;

associate the prescribed drug with a type of pharmacy provider network based on classification of the prescribed drug, the type of pharmacy provider network being an acute medication pharmacy provider network or a maintenance medication pharmacy provider network;

determine whether a pharmacy associated with the claims adjudication data is included within the type of pharmacy provider network associated with the prescribed drug;

adjudicate a pharmacy claim for the prescribed drug through the pharmacy based on the pharmacy claim and a determination of whether the pharmacy is included within the type of pharmacy provider network;

transmit, from the processor over a network, an adjudication response from adjudication based adjudicating the pharmacy claim; and receive, at a pharmacy device of the pharmacy, the adjudication response; and authorizing a filling of the prescription for the member at the pharmacy after receipt of the adjudication response associated with the member to execute a physical filling of the prescription for the member at the pharmacy.

13. The non-transitory machine-readable medium of claim 12, wherein accessing the claims adjudication data includes receiving an adjudication request from a pharmacy relative to the prescribed drug for the member.

14. The non-transitory machine-readable medium of claim 12, wherein classifying the prescribed drug comprises:
analyzing the claims adjudication data to determine one or more of a drug attribute and a fill attribute associated with the prescribed drug.

15. The non-transitory machine-readable medium of claim 12, wherein classifying the prescribed drug comprises:
identifying one of a drug identity, a drug type, and a drug category.

16. The non-transitory machine-readable medium of claim 12, wherein classifying the prescribed drug comprises:
determining that a number of fill requests of the prescribed drug exceeds an acute medication threshold number of fill requests.

17. The non-transitory machine-readable medium of claim 12, wherein the instructions, when executed by the one or more processors, further cause the one or more processors to:
associate a first set member benefits with the prescribed drug for the acute medication pharmacy provider network; and
associate a second set of member benefits with the prescribed drug for the maintenance medication pharmacy provider network.

18. A method for filling a prescription comprising:
receiving, on a processor, a pharmacy claim to adjudicate, the pharmacy claim associated with a member and a prescribed drug;
remotely selecting an acute medication threshold number of available fills, which is a selectable variable;
transmitting the acute medication threshold number of available fills to the processor;
classifying, on the processor, the prescribed drug associated with the member as a maintenance medication based on a determination of whether a number of available fills of the prescribed drug exceeds the acute medication threshold number of available fills;
determining, on the processor, that a pharmacy associated with a request to adjudicate the pharmacy claim is included within an acute medication pharmacy provider network; and
transmitting, on the processor, a warning that a modified set of member benefits are associated with filling the prescribed drug at the pharmacy based on classification of the prescribed drug as a maintenance medication and a determination that the pharmacy is included within the acute medication pharmacy provider network;
transmitting, from the processor over a network, an adjudication response from adjudication based adjudicating the pharmacy claim;
receiving, at a pharmacy device of the pharmacy, the adjudication response;
authorizing a filling of the prescription for the member at the pharmacy after receipt of the adjudication response associated with the member; and
filling the prescription at the pharmacy after receipt of the adjudication response.

19. The method of claim 18, wherein the modified set of member benefits include an elevated member co-pay.

20. The method of claim 18, wherein determining includes transitioning the prescription from the acute medication pharmacy provider network and a maintenance medication pharmacy provider network when the acute medication threshold number is exceeded and filling the prescription using the maintenance medication pharmacy provider network with a different member benefit than a member benefit at the acute medication pharmacy provider network.

21. A pharmacy system for transmitting a prescription comprising:
a plurality of pharmacies including a first pharmacy provider device in an acute medication pharmacy provider network and a second pharmacy provider device in a maintenance medication pharmacy provider network;
a manager device to select, from a variable, an acute medication threshold number of available fills and to transmit the acute medication threshold number of available fills for storage in a database on the memory; and
an adjudicator subsystem including:
a data access device to retrieve, via electronic communication, claims adjudication data associated with a member and a prescribed drug stored in a memory;
an analysis device to determine whether a number of available fills of the prescribed drug exceeds the acute medication threshold number of available fills that is stored in a database on the memory;
a classification device to classify the prescribed drug associated with the member as one of an acute medication and a maintenance medication based on a determination of whether the number of available fills of the prescribed drug exceeded the acute medication threshold number of available fills;
a network determination device to associate the prescribed drug with a type of pharmacy provider network based on classification of the prescribed drug, the type of pharmacy provider network being the acute medication pharmacy provider network or the maintenance medication pharmacy provider network, wherein the network determination device is to determine whether a pharmacy associated with the claims adjudication data is included within the type of pharmacy provider network associated with the prescribed drug;

an adjudication device to adjudicate a pharmacy claim for the prescribed drug through the pharmacy based on the pharmacy claim and a determination of whether the pharmacy is included within the type of pharmacy provider network; and a transmission device to transmit, over an electronic communication network, an adjudication response from the adjudication device based adjudicating the pharmacy claim to at least one of the plurality of pharmacies of either the first pharmacy provider device or the second pharmacy provider device, but not both the first pharmacy provider device and the second pharmacy provider device;

wherein the at least one of the plurality of pharmacies of either the first pharmacy provider device or the second pharmacy provider device is to receive, at a pharmacy device, the adjudication response with an authorization for filling of the prescription for the member; and wherein the at least one of the plurality of pharmacies fills the prescription upon receipt of the adjudication response with an authorization for filling of the prescription.

22. The system of claim 21, wherein the adjudicator subsystem is configured to use criterion for establishing a prescribed drug as an acute medication to be filled in the acute medication pharmacy provider network.

23. The system of claim 22, further comprising a prescriber device to send prescription data over a network without a determination of whether the prescribed drug is an acute drug or a maintenance drug.

* * * * *